United States Patent
Rogozinski

(10) Patent No.: US 7,622,434 B2
(45) Date of Patent: Nov. 24, 2009

(54) SODIUM HYPOCHLORITE GEL COMPOSITION

(76) Inventor: Wallace J. Rogozinski, The Rainbow Lake Club, 1087 Lakeview Ter., Azusa, CA (US) 91702-2455

( * ) Notice: Subject to any disclaimer, the term of this patent is extended or adjusted under 35 U.S.C. 154(b) by 183 days.

(21) Appl. No.: 11/562,691

(22) Filed: Nov. 22, 2006

(65) Prior Publication Data

US 2007/0111911 A1    May 17, 2007

(51) Int. Cl.
*A61K 7/50* (2006.01)
(52) U.S. Cl. .................. 510/130; 510/156; 424/665
(58) Field of Classification Search ........................ None
See application file for complete search history.

(56) References Cited

U.S. PATENT DOCUMENTS

| | | | |
|---|---|---|---|
| 3,666,679 A | 5/1972 | Crotty et al. | |
| 4,035,483 A | 7/1977 | Bunyan | |
| 5,015,228 A | 5/1991 | Columbus et al. | |
| 5,719,197 A | 2/1998 | Kanios et al. | |
| 6,001,141 A | 12/1999 | Quigley | |
| 6,207,201 B1 | 3/2001 | Piacenza | |
| 6,333,054 B1 * | 12/2001 | Rogozinski | 424/661 |
| 6,746,778 B1 | 6/2004 | Negele et al. | |
| 6,748,905 B2 | 6/2004 | Duncan et al. | |
| 6,750,183 B2 | 6/2004 | Gutierrez et al. | |

FOREIGN PATENT DOCUMENTS

CA     2388809      4/2001

OTHER PUBLICATIONS

McDonnell, K.J., et al., "Dakin's Solution Revisited," *The American Journal of Orthopedics*, Jul. 1997, pp. 471-473.
Lineweaver WC, Howard R. Soucy D, et al., "Topical Antimicrobial Toxicity," *Arch Surg*, 120:267-270, 1985.
Kozol, R.A., et al., "Effects of Sodium Hypochlorite Solution (Dakin's Solution) on Cells of the Wound Module," *Arch Surg*, 123:420-423 (1988).
Dow, G., et al., "Infection in Chronic Wounds: Controversies in Diagnosis and Treatment," *Ostomy/Wound Management*, 45(8):23-40 (1999).

* cited by examiner

*Primary Examiner*—Necholus Ogden, Jr.
(74) *Attorney, Agent, or Firm*—MH2 Technology Law Group LLP

(57) ABSTRACT

A gel composition including a sodium hypochlorite solution; at least one viscosity-enhancing agent; and at least one electrolyte is disclosed. Methods of making the composition, methods of disinfecting, and methods of treating are also disclosed.

3 Claims, No Drawings

SODIUM HYPOCHLORITE GEL COMPOSITION

This application claims the benefit of priority under 35 U.S.C. §120 of U.S. application Ser. No. 11/114,148, filed Apr. 26, 2005, now abandoned which is incorporated herein by reference.

FIELD OF THE DISCLOSURE

The present invention relates to compositions for disinfecting substrates, including tissue, and methods of disinfection. The inventive gel composition can comprise a sodium hypochlorite solution, at least one viscosity-enhancing agent, and at least one electrolyte.

BACKGROUND OF THE DISCLOSURE

Sodium hypochlorite has a long and well developed history of use as an antiseptic and disinfecting agent. In 1915, Henry Dakin published his classic investigations of antiseptics in the treatment of battlefield wounds encountered in World War I. He evaluated the antiseptic qualities of chemical agents including: phenol, salicylic acid, hydrogen peroxide, iodine, mercuric chloride, silver nitrate and sodium hypochlorite. However, Dakin preferred sodium hypochlorite and recognized not only "its exceptional antiseptic qualities but also the ability of hypochlorite to debride wounds." See McDonnell, K. J., et al., "Dakin's Solution Revisited," *The American Journal of Orthopedics*, July, 1997, pp. 471-3. Sodium hypochlorite solution in succeeding years became known in the medical community as "Dakin's Solution" and was known for its ability to destroy infection causing microorganisms.

While Dakin's solution has been a mainstay in topical antisepsis for almost 90 years, it has fallen into disuse in recent years because of reports of chemical trauma and cytotoxicity as ascertained by in-vitro laboratory tissue culture investigations. In particular, several studies have shown that the commonly used concentrations of sodium hypochlorite can inhibit host defense cells, such as macrophages, leucocytes and fibroblasts and thereby negatively interfere with the healing process. Moreover, laboratory studies have determined that dilute concentrations of Dakin's solution, such as 0.5%, 0.25% and 0.125% w/w, exhibit cytotoxic properties and can cause tissue damage. See e.g., Lineweaver W C, Howard R. Soucy D, et al., "Topical Antimicrobial Toxicity," *Arch Surg*, 120:267-270, 1985; Kozol, R. A., et al., "Effects of Sodium Hypochlorite Solution (Dakin's Solution) on Cells of the Wound Module," *Arch Surg*, 123:420-423 (1988). It is known that Dakin's solution exhibited cytotoxic properties that inhibited the wound healing process and impaired the host defense mechanism.

Dakin's solution in all concentrations is considered osmotically hypotonic, i.e., it can induce endoosmosis (swelling of tissue and blood cells by an increase in intracellular hydrostatic pressure) possibly causing local tissue stress and edema. Moreover, Dakin's solution diminishes rapidly in antimicrobial effectiveness and chemical activity over the course of its 30 day shelf life limiting its commercial availability to local or hospital pharmacies where it is made fresh to ensure potency. Further, when it is applied topically, it demonstrates a brief duration of action thereby requiring repeated applications to achieve unbroken antisepsis at the wound or burn site.

Based on the work of Lineweaver and others, the use of antiseptic solutions in wounds was discouraged in favor of isotonic saline solution (0.9% sodium chloride) for wound cleansing. The administration of parenteral antibiotics for clinically infected wounds became the standard treatment protocol for all wounds. It was noted, however, in the years following the parenteral antibiotic protocol recommendation that isotonic or normal saline was ineffective in reducing wound bioburden (concentration of microorganisms per gram of tissue), treating a pre-infection state, or treating actual wound infection. Furthermore, a direct link between bacterial wound bioburden and subsequent healing has been established by Dow, G., et al., "Infection in Chronic Wounds: Controversies in Diagnosis and Treatment," *Ostomy/Wound Management*, 45(8):23-40 (1999). It has been quantitatively shown that open wounds can maintain a bioburden of approximately $10^5$ microorganisms without the clinical manifestations of infection. A bioburden of greater than $10^5$ represents a significant challenge for local tissue defenses in the wound environment. A clinical wound infection usually results when $10^6$ or more microorganisms per gram of tissue. As a consequence of these studies, the reduction of wound bioburden became a goal of wound therapy.

The emergence of bacterial resistance to a battery of previously effective antibiotic agents, coupled with an inadequate spectrum of action, and ineffective treatment outcomes, exposed the Achilles heel of antibiotics. Subsequently, topical antiseptics and antimicrobials once again emerged as powerful tools in infection control and wound care.

Prior art antiseptics or disinfectants containing chlorine are typically unsatisfactory for topical applications. Bleach solutions typically comprise high concentrations of caustic soda in order to remain stable and avoid decomposition resulting in a high pH that is injurious to skin and wound tissue. Other commonly used antiseptic agents such as Povidone iodine 10%, Hydrogen Peroxide 3% and Acetic Acid 0.25% all exhibit cytotoxic properties or inhibit neodermal formation.

The pH value of antiseptics or disinfectants containing chlorine can be an important factor in the efficacy of a particular antiseptic or disinfectant's antimicrobial activity. The antimicrobial efficacy of hypochlorite has been experimentally shown to be dependent upon pH. It is generally acknowledged that an increase in pH decreases the biocidal activity of chlorine, whereas a reciprocal decrease in pH increases antimicrobial effectiveness. Known antiseptics or disinfectants containing chlorine, including common hypochlorite solutions, typically have high pH values that are not only injurious to skin and wound tissue, as noted above, but are also less effective in reducing wound bioburden as compared to an antiseptic or disinfectant having a lower pH value.

Thus, there is a need for a composition that overcomes the deficiencies of antiseptics, such as Dakin's solution or other chlorine containing disinfectants.

SUMMARY OF THE DISCLOSURE

According to various aspects of the disclosure, there is provided a gel composition comprising a sodium hypochlorite solution; at least one viscosity-enhancing agent; and at least one electrolyte, wherein the gel composition has a pH value ranging from about 10.4 to about 11.

According to various aspects of the disclosure, there is provided a method of topically disinfecting a substrate comprising applying to the substrate an effective amount of a composition comprising a sodium hypochlorite solution; at least one viscosity-enhancing agent; and at least one electrolyte, wherein the composition has a pH value ranging from about 10.4 to about 11.

According to various aspects of the disclosure, there is provided a method of treating a topical infection comprising applying to a patient in need thereof an effective amount of a disinfectant composition comprising a sodium hypochlorite solution; at least one viscosity-enhancing agent; and at least one electrolyte, wherein the disinfectant composition has a pH value ranging from about 10.4 to about 11, to the infected area and/or the surrounding infected area.

According to various aspects of the disclosure, there is provided a method of treating a heavily contaminated or infected wound comprising applying to a patient in need thereof an effective amount of a composition comprising a sodium hypochlorite solution; at least one viscosity-enhancing agent; and at least one electrolyte, wherein the composition has a pH value ranging from about 10.4 to about 11, to the contaminated or infected wound and/or the surrounding contaminated or infected area.

According to various aspects of the disclosure, there is provided a method of disinfecting an intact skin site prior to a surgical or invasive procedure comprising applying to a patient in need thereof an effective amount of a composition comprising a sodium hypochlorite solution; at least one viscosity-enhancing agent; and at least one electrolyte, wherein the composition has a pH value ranging from about 10.4 to about 11.

According to various aspects of the disclosure, there is provided a method for making a gel composition comprising combining at least one viscosity-enhancing agent with water; combining sodium hypochlorite with USP purified water; combining the sodium hypochlorite solution from (b) with the viscosity-enhancing solution from (a) to form a thickened solution; and combining at least one electrolyte with the thickened solution to form the gel composition, wherein the gel composition has a pH value ranging from about 10.4 to about 11.

It is to be understood that both the foregoing general description and the following description of various embodiments are exemplary and explanatory only and are not restrictive.

DESCRIPTION OF VARIOUS EMBODIMENTS

The disclosed composition can be safe and effective, broad spectrum, topical agents with at least one of the following properties: bacteriocidal, fungicidal and virucidal properties. Moreover, the composition can be in the form of a biologically compatible, non-traumatizing and non-cytotoxic, thixotropic, aqueous gel. The disclosed composition can also embody an osmotic potential thereby rendering it isotonic.

The disclosed composition can provide a method for treating skin sites or wounds that harbor infection-causing microorganisms. The composition can interfere with the microorganisms' reproductive mechanisms. This has the effect of inhibiting their multiplication and/or causing their death. The composition can therefore prevent and/or treat infectious disease without suppressing host defenses and/or exhibiting cytotoxic properties. The composition disclosed herein can also absorb wound exudates and other serosanguineous fluids that support the growth of pathogenic microorganisms, as well as cause the maceration of the skin around the wound margin that can retard healing. Moreover, the disclosed composition can also provide a method for maintaining the peripheral area around endogenous devices, such as intravenous and urinary indwelling catheters and/or any medical device that breaches the skin, vascular system or urinary tract free of infectious microorganisms.

The disclosed composition can also reduce the numbers of microorganisms that constitute a preinfection state (wound bioburden) to host manageable levels so that a natural sequence of wound healing can occur. Moreover, the composition can provide a sustained duration of antimicrobial action and to assist in maintaining a moist wound environment.

The disclosed composition can comprise a sodium hypochlorite solution, at least one viscosity-enhancing agent, and at least one electrolyte. The composition can maintain a useful shelf-life of at least 2 years.

The sodium hypochlorite solution can be prepared by any method known to one of ordinary skill in the art. In an embodiment, the sodium hypochlorite solution can be prepared by mixing commercially available sodium hypochlorite with USP purified water. For example, a concentration from about 5% to about 18%, for example from about 7% to about 15%, and as a further example from about 9% to about 13% by weight of commercially available sodium hypochlorite can be dispersed in USP purified water so that the resultant sodium hypochlorite solution comprises from about 0.0125% to about 1%, for example from about 0.1% to about 0.8%, by weight of sodium hypochlorite. Commercially available sodium hypochlorite can be available from Spectrum Chemical, Gardena, Calif. In another embodiment, the sodium hypochlorite solution is not prepared by partial electrolysis of a sodium chloride solution.

The sodium hypochlorite solution can vary in both pH and available chlorine. As used herein, "available chlorine" refers to the amount of elemental chlorine, hypochlorous acid, and hypochlorite ion, in solution. The variance in available chlorine can depend upon pH. As pH increases, hypochlorous acid dissociates into hydrogen and hypochlorite ion. The dissociation of hydrochlorous acid can depend upon the pH and the equilibrium between hydrochlorous acid and hypochlorite ion.

The disclosed composition can have a pH value ranging from about 10.4 to about 11. The disclosed composition can provide a potent antimicrobial agent that is not injurious to skin or wound tissue. Additionally, when applied to skin, the disclosed composition can approximate the natural pH of skin, thereby maintaining its natural antimicrobial integrity.

The composition disclosed herein can also comprise at least one viscosity-enhancing agent. The term "viscosity-enhancing agent" refers to any agent that, when applied in various concentrations in an aqueous medium, results in the formation of stable hydrogels that exhibit thixotropic properties. The at least one viscosity-enhancing agent can be chosen from natural clay and synthetic clay. In an embodiment, the hydrogel viscosity can be achieved by the use of an entirely synthetic mineral which is akin to the natural clay mineral hectorite in structure and composition. Unlike natural clay, a synthetic mineral is typically free of impurities yet can be equal in structure to natural hectorite. One such synthetic mineral is listed in the American Chemical Society's Chemical Abstracts Service (CAS) under the name sodium lithium magnesium silicate (Registration No. 53320-86-8) and in the Cosmetic, Toiletries and Fragrance Association (CTFA) dictionary as sodium magnesium silicate. This synthetic mineral is sold commercially under the trade name LAPONITE®, a registered trademark of Southern Clay Products, Inc., Gonzales, Tex. Other non-limiting examples of the at least one viscosity-enhancing agent include magnesium aluminum silicates, smectite clays, and an amorphous clay mineral, such as allophone; two-layer type crystalline clay minerals, such as equidimensional crystal, kaolinite, and nacarite; elongate crystals, such as halloysites; three-layer type crystalline clay minerals, such as sodium montmorillonite, calcium montmorillonite, sauconite, vermiculite, nontronite, saponite, hectorite, and bentonite; chain structure crystalline clay minerals, such as attapulgite, sepiolite, and palygorskite; and mixtures thereof.

Two-layer type crystalline clay minerals can be sheet structures composed of units of one layer of silica and one layer of alumina octahedrons. Three-layer type crystalline clay minerals can be sheet structures composed of two layers of silica tetrahedrons and one central dioctahedral or trioctahedral layer. The chain structure crystalline clay minerals are hornblende-like chains of silica tetrahedrons linked together by octahedral groups of oxygen and hydroxyls containing aluminum and magnesium atoms.

In an embodiment, the at least one viscosity-enhancing agent can conform to the empirical formula $Na_{0.7+}((Si_8Mg_{5.5}Li_{0.3})O_{20}(OH_4))^{-0.7}$. The at least one viscosity-enhancing agent can serve as the gel matrix once ionic bonding has been completed.

The at least one viscosity-enhancing agent can be present in the composition in any desired or effective amount, such as from about 0.1% to about 10%, for example from about 0.5% to about 8%, and, as a further example, from about 1% to about 5% by weight with respect to the total weight of the composition. By varying the concentration of the at least one viscosity-enhancing agent, the gel composition can have consistencies that range from a heavy liquid to a thick, slightly cloudy gel.

Without being limited to any particular theory, it is believed that the swelling properties of the natural and synthetic clay minerals permit colloidal particles to form upon hydration. These colloidal particles can exhibit repulsive electrical surface charges, which can then be able to maintain a uniform suspension in solution. With the addition of an ionic compound, such as, for example, USP sodium chloride, USP potassium chloride, to the colloidal suspension, the repulsive particle charges can be reduced significantly, allowing the formation of a viscous, aqueous gel with rheologocial characteristics that can be typical of the clay mineral used. The formed gel can demonstrate at least one property such as the flow properties and the rheological behavior classically termed thixotropic, wherein a semi-solid gel can be induced by shaking or stirring, to become a sol (a thin liquid) and revert once again to a semi-solid gel upon standing.

In an embodiment, at least one organic modifier can be combined with the at least one viscosity-enhancing agent in order to realize the best properties of both. The at least one viscosity-enhancing agent and the at least one organic modifier can be used in a combination, such as an approximate ratio of about 4 parts of at least one viscosity-enhancing agent to about 1 part of at least one organic modifier. The at least one organic modifier can generally be cellulosic in nature, and can typically be used in the art to form thixotropic gels. Non-limiting examples of the at least one organic modifier include hydroxypropyl methyl cellulose, guar hydroxypropyl trimonium chloride, carbomer, xanthan gum, polyethylene glycol (PEG) block polymers, and polyvinylpyrrolidone.

The composition disclosed herein can also comprise at least one electrolyte. The at least one electrolyte can decrease or increase the ionic bond strength of the at least one viscosity-enhancing agent. In various embodiments, the at least one electrolyte is different from the sodium hypochlorite solution.

In various embodiments, the at least one electrolyte can be chosen from USP sodium chloride, NF hydrochloric acid, and USP citric acid. Other compounds, including alkali metal and alkali earth metal salts that dissociate into electrolytes such as the salts of potassium, magnesium, and calcium can also be used to initiate ionic bonding in the formation of thixotropic gels. Alternative electrolytes can produce gels with properties equivalent to those utilizing USP sodium chloride.

The at least one electrolyte can be present in the composition in any desired or effective amount, such as from about 0.01% to about 10%, for example, from about 0.1% to about 5%, and as a further example from about 1% to about 3% by weight with respect to the total weight of the composition.

The gel composition can have a wide variety of uses, including the effective treatment of topical bacterial and fungal infections, the treatment of heavily contaminated or infected wounds, and the preparation of an intact skin site prior to a surgical or invasive procedure.

A topical infection can be understood by those of ordinary skill in the art to refer generally to a minor infection, bacterial and/or fungal in nature, which can be typically superficial and localized.

A heavily contaminated wound can be understood by those of ordinary skill in the art to mean a wound that is heavily contaminated by micro-organisms, but not clinically infected. Such wounds can be often characterized by a prolonged period of inflammation, as well as a delay in wound healing or repair. Heavily infected wounds can be understood by those of ordinary skill in the art to mean wounds with a bioburden greater than $10^5$ microorganisms per gram of tissue.

The rheological characteristics of thixotrophy, in which the apparent viscosity decreases as the system is disturbed by stirring or shaking and then reverses during periods of dormancy, can be useful in the administration and use of the composition described herein. The ability to apply a product to the skin with the use of simple delivery devices such as pump sprayers and squeeze tubes can eliminate the characteristic disadvantages of dispensing thin liquids and thick gels, where thin liquids cannot be contained at the treatment site and permanently thick gels cannot be easily dispensed. The rheological phase shift from gel to sol to gel can provide product administration latitude.

EXAMPLES

The following examples are illustrative and are non-limiting to the present teachings.

Manufacturing Method for Gel Composition 0.1% to 10% w/w Laponite® was slowly added to USP purified water under vigorous agitation and mixed until the Laponite® was fully hydrated and a uniform, viscous liquid formed and appeared clear.

A commercially available sodium hypochlorite solution in a concentration from 5% to 18% was dispersed in an aliquat of USP purified water under vigorous agitation and mixed until completely dissolved to achieve a final concentration in the range of 0.0125% to 1% w/w.

0.01% to 10% w/w of USP sodium chloride was very slowly added to the Laponite® and sodium hypochlorite mixture under continuous and vigorous agitation. Viscosity of the mixture increased immediately and the final composition formed a clear to slightly hazy, thick, semi-solid hydrogel. The pH of the final composition ranged from about 10.4 to about 11.0.

In comparison, the pH of a hydrogel composition comprising sodium hypochlorite prepared by electrolytic methods such as electrolytic chloroxidation ranges from about 9.7 to about 10.3.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "an electrolyte" includes two or more different electrolytes. As used herein, the term "include" and its grammatical variants are intended to be non-limiting, such that recitation of items in a list is not to the exclusion of other like items that can be substituted or added to the listed items.

The references cited herein are incorporated by reference in their entirety.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A gel composition comprising:
   (a) a sodium hypochlorite solution that is not prepared by the partial electrolysis of a sodium chloride solution;
   (b) at least one viscosity-enhancing agent chosen from magnesium aluminum silicates, smectite clays, allophone, kaolinite, nacarite, halloysites, sodium montmorillonite, calcium montmorillonite, sauconite, vermiculite, nontronite, saponite, hectorite, bentonite, attapulgite, sepiolite, palygorskite, and mixtures thereof; and
   (c) at least one electrolyte chosen from USP sodium chloride, USP citric acid, and NF hydrochloric acid,
   wherein the gel composition has a pH value ranging from about 10.4 to about 11;
   wherein the sodium hypochlorite is present in the gel composition in an amount ranging from about 0.0125% to about 1% by weight with respect to the total weight of the gel composition;
   wherein the at least one viscosity-enhancing agent is present in the composition in an amount ranging from about 0.1 to about 10% by weight relative to the total weight of the composition; and
   wherein the at least one electrolyte is present in the composition in an amount ranging from about 0.01 to about 10% by weight relative to the total weight of the composition.

2. The composition of claim 1, wherein the sodium hypochlorite is present in the gel composition in an amount ranging from about 0.1% to about 0.8% by weight with respect to the total weight of the gel composition.

3. The composition of claim 1, wherein the at least one viscosity-enhancing agent further comprises at least one organic modifier.

* * * * *